United States Patent
Drent et al.

(10) Patent No.: US 6,818,797 B2
(45) Date of Patent: Nov. 16, 2004

(54) PROCESS FOR THE HYDROFORMYLATION OF ETHYLENICALLY UNSATURATED COMPOUNDS IN THE PRESENCE OF AN ACID AND A MONO TERT-PHOSPHINE

(75) Inventors: Eit Drent, Amsterdam (NL); Willem Wabe Jager, Amsterdam (NL)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 10/737,651

(22) Filed: Dec. 16, 2003

(65) Prior Publication Data

US 2004/0152923 A1 Aug. 5, 2004

(30) Foreign Application Priority Data

Dec. 17, 2002 (EP) .............................. 02258670

(51) Int. Cl.[7] .............................................. C07C 45/50
(52) U.S. Cl. ...................................... 568/451; 568/454
(58) Field of Search ................................ 568/451, 454

(56) References Cited

U.S. PATENT DOCUMENTS

| 3,418,351 A | | 12/1968 | Greene et al. ............. 260/439 |
| 5,004,823 A | | 4/1991 | Devon et al. ............... 556/136 |
| 5,488,174 A | * | 1/1996 | Drent et al. ................. 568/454 |
| 5,994,591 A | | 11/1999 | Arnoldy et al. ............. 568/454 |
| 6,037,506 A | | 3/2000 | Bolinger ..................... 568/909 |

FOREIGN PATENT DOCUMENTS

| EP | 0273489 A2 | 11/1987 | ........... C07C/67/38 |
| EP | 0350921 A1 | 7/1989 | ........... C07C/45/50 |
| EP | 0489472 A2 | 11/1991 | ........... C07C/51/14 |
| WO | WO 95/05354 | 2/1995 | ........... C07C/29/16 |

\* cited by examiner

*Primary Examiner*—Samuel Barts
*Assistant Examiner*—Sikarl A. Witherspoon

(57) ABSTRACT

The invention pertains to a process for the hydroformylation of an ethylenically unsaturated compound in the presence of an acid with a pKa<+3, and a catalyst of a group VIII metal and a bidentate ligand of the formula:

$$R_1R_2\text{—P—X—P—}R_3R_4 \qquad (I)$$

wherein P is a phosphorus atom, X represents a bivalent organic bridging group, $R_1$, $R_2$, $R_3$ and $R_4$ represent independently a substituted or unsubstituted hydrocarbyl group, or $R_1$ and $R_2$ together with the phosphorus atom to which they are bonded and/or $R_3$ and $R_4$ together with the phosphorus atom to which they are bonded represent a bivalent substituted or unsubstituted cyclic group, characterized in that the process is performed in the presence of a mono tert-phosphine, wherein the ratio moles of mono tert-phosphine:moles of acid is from about 1:1 to about 10:1.

11 Claims, No Drawings

PROCESS FOR THE HYDROFORMYLATION OF ETHYLENICALLY UNSATURATED COMPOUNDS IN THE PRESENCE OF AN ACID AND A MONO TERT-PHOSPHINE

FIELD OF THE INVENTION

The invention relates to a process for the hydroformylation of an ethylenically unsaturated compound in the presence of an acid with a pKa<+3, and a catalyst of a group VIII metal and a bidentate ligand.

BACKGROUND OF THE INVENTION

Processes for the hydroformylation of ethylenically unsaturated compounds are known in the art. In U.S. Pat. No. 5,004,823 the hydroformylation of olefins with rhodium complex were described. The new class of rhodium catalysts allows the use of low pressure and leads to high yield of product.

In EP 273,489 a process was disclosed for the selective carbonylation of conjugated dienes in the presence of a specific palladium compounds with a multidentate organic phosphorus ligand. According to this process also monodentate phosphorus compounds may be present. This process aimed at high conversion rates and less corrosion problems.

In EP 489,472 a carbonylation process was disclosed of ethylenically unsaturated compounds in the presence of a palladium catalyst, a monodentate phosphine, and an anion of derived from an acid with pKa<+3 to maintain a high reaction as well as conversion rate.

In U.S. Pat. No. 5,994,591 a hydroformylation process was disclosed in the presence of a palladium, platinum, or nickel catalyst, a bidentate ligand, and anion other than halide anions to obtain a process for effectively removing the catalyst in a solventless evaporation product separation system without affecting the effectiveness of the catalyst.

In U.S. Pat. No. 6,037,506 a process was presented with a palladium, platinum, or nickel catalyst, a bidentate ligand, an acid, and a promoter comprising a formate or formic acid reagent. This process leads to less damage of the reactor. It was further reported that this process reduces the paraffin make.

Generally, such processes are conducted by introducing the various reactants into the reactor and allowing the reaction to proceed under the desired reaction conditions. The disclosed methods, however, suffer from a few disadvantages, i.e. the occurrence of solid particles on the liquid-liquid interface of the immiscible liquid phases (plating), and in many instances also the formation of paraffin side-products. These lead to decreased yields and cumbersome isolation procedures. Plating leads to loss of active catalyst during the process, and since the catalyst by far is the most expensive constituent of the reaction mixture plating effects are commercially unattractive. Therefore, in one aspect of the present invention plating is prevented effectively and the advantageous properties of the prior art methods are maintained.

SUMMARY OF THE INVENTION

To this end an anti-plating process was found for the hydroformylation of an ethylenically unsaturated compound process in the presence of an acid with a pKa<+3, and a catalyst of a group VIII metal and a bidentate ligand of the formula:

$$R_1R_2\text{—P—X—P—}R_3R_4 \quad (I)$$

wherein P is a phosphorus atom, X represents a bivalent organic bridging group, $R_1$, $R_2$, $R_3$ and $R_4$ represent independently a substituted or unsubstituted hydrocarbyl group, or $R_1$ and $R_2$ together with the phosphorus atom to which they are bonded and/or $R_3$ and $R_4$ together with the phosphorus atom to which they are bonded represent a bivalent substituted or unsubstituted cyclic group, characterized in that the process is performed in the presence of a mono tert-phosphine, wherein the ratio moles of mono tert-phosphine:moles of acid is from about 1:1 to about 10:1.

In addition to the effective anti-plating properties of the above process another aspect of the present invention provides a method for reducing paraffin make. By using a mixture of at least two acids wherein one of the acids has a pKa<-3, and another acid has a pKa value between -3 and +3, the paraffin make is strongly reduced. By using such a mixture of acids without the addition of the mono tert-phosphine compound the paraffin make is also effectively reduced. However, the advantageous anti-plating effects are no longer observed.

DETAILED DESCRIPTION OF THE INVENTION

In the context of this invention the term "bivalent organic bridging group" means any bridging group such as an alkylene, alkylidene, cycloalkylidene, arylene, and the like. These groups may be substituted with common substituents such as alkyl, alkoxy, cycloalkyl, aryl, N-heterocyclic group, or halogen, and the like, may be branched or unbranched, and may contain heteroatoms, such as oxygen and nitrogen, or may contain substituents with carbonyl groups. In general such alkyl groups will have up to 20 carbon atoms, any cycloalkyl groups will have from 5-7 carbon atoms in the ring structure and any aryl group will have up to 18 carbon atoms in the ring structure. Conveniently, the aryl group may be an anthryl, naphthyl or, which is preferred, a phenyl group. The heterocyclic ring may be a single heterocyclic ring or may be a part of an optionally substituted larger, condensed ring structure as exemplified by pyridyl, pyrazinyl, quinolyl, isoquinolyl, pyrimidyl, pyridazinyl, indolizinyl, cinnolinyl, acridinyl, phenazinyl, phenanthridinyl, phenanthrolinyl, phthalazinyl, naphthyridinyl, quinoxalinyl and quinazolinyl groups. The term "substituted or unsubstituted hydrocarbyl group" means a hydrocarbyl group, which is saturated, unsaturated, cyclic, acyclic, or aromatic. The hydrocarbyl group may be substituted with the common substituents, may contain heteroatoms and/or carbonyl groups.

The "bivalent substituted or unsubstituted cyclic group" is together with the phosphorus atom a bicyclic structure.

The source of the group VIII metal (catalyst component) preferably is selected from cationic compounds, such as for example the salts of the group VIII metal with, for instance, nitric acid, sulfuric acid, or alkane carboxylic acids having not more than 12 carbon atoms. Salts of hydrohalogenic acids may, in principle, be used as well as they provide a further reduction of the paraffin make. Especially halide ions selected from chloride, bromide, and iodide, and mixtures thereof which have proved to be beneficial in this respect. Moreover, group VIII metal complexes may also be used, for instance the group VIII metal acetyl acetonate, tetrakis (triphenylphosphine) group VIII metal, bis(tri-o-tolylphosphine) group VIII metal acetate or bis (triphenylphosphine) group VIII metal sulfate. Metallic group VIII metal may be used if the catalyst composition comprises an acid component. Preferred group VIII metals are selected from palladium and platinum.

The bidentate catalyst preferably has the formula $R_1R_2$—P—X—P—$R_3R_4$, wherein P is phosphorus, X is a hydrocarbyl group, which may be substituted, and $R_1$ and $R_2$ together with the phosphorus atom to which they are bonded, and $R_3$ and $R_4$ together with the phosphorus atom to which they are bonded represent a bivalent substituted or unsubstituted cyclic group. Typically, these bicyclic structures have 5 to 8 carbon atoms. The ring may further contain unsaturated bonds and may be substituted with alkyl, alkoxy, aryl, aralkyl, and halogen groups. Typical examples of bivalent cyclic phosphines comprise at least 5 ring atoms, and preferably 6 to 9 ring atoms. More preferably the cyclic bridging groups contains 8 ring atoms. Apart from the phosphorus atom all atoms are usually carbon atoms, but one or two carbon atoms may also be replaced by a heteroatom, such as oxygen or nitrogen atoms. Examples of suitable cyclic groups are 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene, 2,6-dimethyl-1,5-cyclooctylene, and limonenylene. Most preferably, the $R_1R_2$—P and $R_3R_4$—P moieties comprise the bicyclononylphosphinyl group, i.e. a preferred bicyclic ligand is:

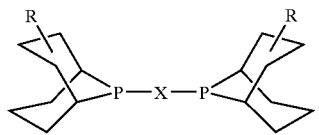

wherein X is a hydrocarbyl group selected from alkylene, cycloalkylene, and arylene, which may be substituted, and R is H or a substituent selected from alkyl, alkoxy, halogen, aryl, aralkyl, and a carbonyl-containing group.

The term "mono tert-phosphine" means a trisubstituted phosphine, each of the substituents preferably being independently a hydrocarbyl group, such as alkyl, cycloalkyl, aryl, or aralkyl group. Preferred trihydrocarbylphosphines are triarylphosphine and trialkylphosphine. Most preferred is triphenylphosphine.

Acids having a pKa<+3 (measured in water at 18° C.) are used in the process of the invention and include Lewis acids such as, for example, $BF_3$, $AsF_5$, $SbF_5$, $PF_5$, $TaF_5$, or $NbF_5$, Bronsted acids such as, for example, a hydrohalogenic acid, in particular HF, phosphoric acid or sulfuric acid. Specific examples of the last-named type of acids are fluorosilicic acid, $HBF_4$, $HPF_6$, and $HSbF_6$. Particularly suitable is trifluoromethanesulfonic acid.

When a mixture of acids is used, one of the acids has a pKa value between −3 and +3, which can form a coordination bond with the group VIII metal. Particularly useful are, for instance, sulfonic acids. Very suitable sulfonic acids include alkylsulfonic acids, especially linear alkylsulfonic acids, alkarylsulfonic acids such as alkylbenzenesulfonic acids, alkyltoluenesulfonic acids and alkylxylenesulfonic acids, and hydroxyalkylsulfonic acids, e.g. alpha- or beta-hydroxyalkylsulfonic acids.

Typical sulfonic acids that can be used are methanesulfonic acid, fluorosulfonic acid, chlorosulfonic acid, and p-toluenesulfonic acid, the methanesulfonic acid being preferred. Sulfonic acids as mentioned hereinbefore are readily available in the form of the corresponding sulfonates, and especially the alkali metal sulfonate, as such compounds are well known for their detergent properties. A particularly useful mixture of acids comprises a mixture of trifluoromethanesulfonic acid and methanesulfonic acid.

It is advantageous to perform the process in the presence of a halide anion selected from chloride, bromide, and iodide, and mixtures thereof. This further reduces the paraffin make. These halide anions can be added as a salt, for instance as an alkali or earth alkali metal salt.

The stoichiometry of the total amount of mono tert-phosphine and acid during the reaction should be so that the ratio moles of mono tert-phosphine:moles of acid is from about 1:1 to about 10:1. Preferably, this ratio is about 1.05:1 to about 5:1.

The quantity of group VIII metal, as used as catalyst component in the process of the invention, is not critical. Preference is given to the use of quantities in the range between about $10^{-3}$ and about $10^{-7}$ grams of atom metal per mole of ethylenically unsaturated compound.

In general the amount of phosphine ligand to be employed in the catalyst composition for use in the process of the present invention is not critical and may vary over wide ranges, which ranges may sometimes also be related to the type of phosphine ligand. For example, bidentate diphosphines will generally be employed in a quantity of about 0.5–3 moles per gram atom of palladium.

The ethylenically unsaturated compound may be an unsubstituted or substituted linear, branched or cyclic compound preferably having 2–30, and in particular 2–20, carbon atoms and preferably 1–3 double and/or triple bonds. The unsaturated compounds may be substituted, for instance, with one or more halogen atoms or cyano, ester, alkoxy, hydroxy, carboxyl, or aryl groups. If the substituents are not inert under the reaction conditions, the hydroformylation reaction may be accompanied with other reactions. Examples of suitable olefinic compounds are ethene, propene, butene-1, butene-2, isobutene, cyclopentenes, the isomeric pentenes, hexenes, octenes and dodecenes, 1,5-cyclooctadiene, cyclododecene, 1,5,9-cyclododecatriene, allyl alcohol, methyl acrylate, ethyl acrylate, methyl methacrylate, acrylonitrile, acrylamide, N,N-dimethyl acrylamide, vinyl chloride, allyl chloride, acrolein, oleic acid, methyl allyl ether, and styrene. Examples of suitable acetylenes include propyne, 1-butyne, 2-butyne, 1-pentyne, 1-hexyne, 1-heptyne, 1-octyne, 2-octyne, 4-octyne, 5-methyl-3-heptyne, 4-propyl-2-pentyne, 1-nonyne, phenylethyne, and cyclohexylethyne.

In the process according to the invention the carbon monoxide may be used pure or diluted with an inert gas, such as nitrogen, noble gases, or carbon dioxide. The ratio moles of carbon monoxide:moles of hydrogen usually ranges from about 1:10 to about 10:1.

The hydroformylation according to the invention is preferably carried out at a temperature in the range between about 50 and about 200° C., in particular between about 75 and about 150° C. The overall pressure preferably is between about 1 and about 100 bar, in particular about 20 and about 75 bar gauge.

The process according to the invention is preferably performed in a two-phase liquid reaction medium, wherein the term "two-phase liquid reaction medium" refers to a reaction medium which is at least a two-phase, or more generally a multi-phase liquid, reaction medium at the beginning of the reaction and during the early stages thereof.

The process according to the present invention may be carried out batchwise, continuously or semi-continuously.

The compounds prepared according to the process of the present invention may conveniently be isolated from the reaction mixture by known techniques, such extraction or distillation.

A preferred group of compounds to be prepared by the process of the present invention are alcohols and especially those alcohols containing 8–30 carbon atoms. Such full esters are valuable products for use as lubricants, detergents and plasticizers. Other products, which may be prepared by the present process, may be used as precursors for the preparation of esters, ethers, or other fine chemicals.

The invention will be further illustrated with the following examples:

EXAMPLE 1

A 350 ml magnetically stirred Hastelloy C autoclave was charged with 30 ml of 2-ethyl hexanol, 20 ml of linear octenes (thermodynamically equilibrated) and a solution of 10 ml of sulfolane/0.5 ml water containing 0.25 mmole of $Pd(OAc)_2$, 0.4 mmole of 1,2-P,P'-bis(9-phosphabicyclo[3.3.1]nonyl) ethane ("DIRC-2"), 0.5 mmole of $CF_3SO_3H$, and 0.1 mmole of HCl.

The autoclave was closed and after being flushed with carbon monoxide, pressurized with carbon monoxide to a partial pressure of 20 bar and hydrogen to a partial pressure of 40 bar. Subsequently, the autoclave was sealed and the contents were heated to a temperature of 100° C. and maintained at this temperature for 5 hours. The initial rate of hydroformylation, defined as the average rate of carbon monoxide/hydrogen consumption over, the first 30% conversion amounted 1200 mole/mole Pd/h. After cooling to room temperature, the reaction mixture consisted of two layers, a lower sulfolane catalyst-containing layer and an upper alcohol-containing (ethyl hexanol/nonanols) layer. A trace of Pd black was visible at the interface of the two layers (estimated 5% of Pd content). A sample of the final reaction mixture (5 hour total reaction time) was taken from the upper layer and analyzed by GLC (Gas Liquid Chromatography). Complete conversion of the octenes was found and the selectivity to nonanol alcohols was 99% (linearity 72%) with selectivity to paraffin of 0.7%.

EXAMPLE 2

This example was performed as Example 1, but now 1 mmole of $P(Bu)_4CH_3SO_3$ was added to the catalyst solution of Example 1. An initial rate of 1100 mole/mole Pd/hour was observed. GLC analysis of the upper alcohol-containing layer (after 5 hour total reaction time) showed complete conversion of the octenes and a selectivity to nonanols of 99% with a linear nonanol (1-nonanol) content of 73%. Paraffin selectivity was only 0.2%. A trace of Pd black was observed at the alcohol/sulfolane interface. This example shows that addition of a phosphonium salt with anions derived from an acid with +3>pKa>−3 leads to lower paraffin make.

EXAMPLE 3

Performed as Example 1, but the catalyst/sulfolane solution now contained 0.25 mmole of $Pd(OAc)_2$, 0.4 mmole of DIRC-2, 0.6 mmole of triphenyl phosphine and 1.0 mmole of $CF_3SO_3H$. An initial rate of hydroformylation of 1400 mole/mole Pd/hour was found. GLC analysis of the upper layer (after 5 hour total reaction time) showed complete conversion of octenes and a selectivity to nonanols of 98% with 1.0% to paraffin (octane). Linearity of nonanols produced was 72%. No Pd metal at the interface between alcohol and sulfolane was visible.

This example shows that addition of monophosphine and very strong acid (pKa<−3) leads to reduced Pd metal formation, but also leads to a slight increase of paraffin selectivity.

EXAMPLE 4

Performed as Example 3, but 1.0 mmole of $CF_3SO_3H$ was replaced by a mixture of 0.5 mmole of $CH_3SO_3H$ and 0.5 mmole of $CF_3SO_3H$. An initial rate of hydroformylation of 1200 mole/mole Pd/hour was observed. Complete conversion of octenes was observed in the final reaction mixture (5 hour reaction time). Alcohol selectivity of 99% with paraffin selectivity of 0.36% was observed. No Pd black was visible at the alcohol/sulfolane interface. Comparison with Example 1 shows that addition of monophosphine and acid with +3>pKa>−3 leads to both reduced Pd metal formation and reduction of paraffin selectivity, while maintaining high reaction rates.

EXAMPLE 5

Performed as Example 1, but in the catalyst solution, 0.4 mmole of "DIRC-2" was replaced by 0.4 mmole of meso-3,4-P,P'-bis(9-phosphabicyclo[3.3.1]nonyl)butane and hydroformylation was carried out at 110° C. instead of 100° C. An initial hydroformylation of 400 mole/mole Pd/hour was observed. An octene conversion of nearly 100% was found at the end of the hydroformylation period (5 hour). An alcohol selectivity of 88% (linearity 74%) with a paraffin selectivity of 6.6% was obtained. Higher esters, mainly 2-ethylhexanol esters of nonanoic acids were co-produced in an amount of about 5%. A trace of Pd black could be observed at the alcohol/sulfolane surface. This example shows that with a derivative "DIRC-2" ligand, containing methyl-substituents at the bridge carbon atoms, a lower selectivity to alcohols was obtained, in particular paraffin selectivity and ester selectivity was significantly higher than with the parent ligand.

EXAMPLE 6

Performed as in Example 5, but now 0.6 mmole of triphenyl phosphine and 0.5 mmole of $CH_3SO_3H$ were added to the catalyst solution of Example 5. The initial hydroformylation rate was 400 mole/mole Pd/hour. An alcohol selectivity of 92% (linearity 73%) with a paraffin selectivity of 2.0% was obtained. Higher esters, mainly 2-ethyl hexanol esters of nonanoic acids were produced in a selectivity of about 6%. No Pd black precipitate could be observed at the alcohol/sulfolane interface. Comparison with Example 5 showed that addition of monophosphine and an acid of +3>pKa>−3 leads to reduced Pd black formation and reduced paraffin selectivity. This example showed that according to the invention, the addition of monophosphine and acid with +3>pKa>−3 leads to reduced Pd black formation as well as reduced paraffin selectivity.

EXAMPLE 7

Performed as in Example 4, but now 0.5 mmole of $CH_3SO_3H$ were omitted in the catalyst composition. Hydroformylation proceeded with a low rate of <100 mole/mole Pd/hour. Only partial conversion (30%) of the octenes was reached after 5 hours. No Pd metal formation was observed. This example showed that although addition of monophosphine leads to reduced Pd black formation, the simultaneous addition of acid is required to maintain high reaction rate.

We claim:

1. A process for the hydroformylation of an ethylenically unsaturated compound in the presence of an acid with a pKa<+3, and a catalyst of a group VIII metal and a bidentate ligand of the formula:

$$R_1R_2\text{—P—X—P—}R_3R_4 \qquad (I)$$

wherein P is a phosphorus atom, X represents a bivalent organic bridging group, $R_1$, $R_2$, $R_3$ and $R_4$ represent independently a substituted or unsubstituted hydrocarbyl group, or $R_1$ and $R_2$ together with the phosphorus atom to which they are bonded and/or $R_3$ and $R_4$ together with the phosphorus atom to which they are bonded represent a bivalent substituted or unsubstituted cyclic group, characterized in that the process is performed in the presence of a mono tert-phosphine, wherein the ratio moles of mono tert-phosphine:moles of acid is from about 1:1 to about 10:1.

2. The process according to claim 1 wherein the process is performed in a mixture of at least two acids, at least one acid having a pKa<−3 and at least one acid having a pKa between −3 and +3.

3. The process according to claim 1 wherein the process is performed in the presence of a halide anion selected from chloride, bromide, and iodide, and mixtures thereof.

4. The process according to claim 1 wherein the bidentate ligand has the formula $R_1R_2$—P—X—P—$R_3R_4$, wherein P is phosphorus, X is a bivalent hydrocarbyl group, which may be substituted, and $R_1$ and $R_2$ together with the phosphorus atom to which they are bonded, and $R_3$ and $R_4$ together with the phosphorus atom to which they are bonded represent a bivalent substituted or unsubstituted cyclic group.

5. The process according to claim 4 wherein the ligand is:

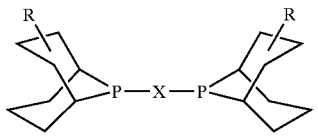

wherein X is a bivalent hydrocarbyl group selected from alkylene, cycloalkylene, and arylene, which may be substituted, and R is H or a substituent selected from alkyl, alkoxy, halogen, aryl, aralkyl and a carbonyl-containing group.

6. The process according to claim 1 wherein the group VIII metal is selected from Pd and Pt.

7. The process according to claim 1 wherein the mono tert-phosphine is a trihydrocarbylphosphine.

8. The process of claim 7 wherein the trihydrocarbyl phosphine is selected from the group consisting of triarylphosphine and trialkylphosphine.

9. The process according to claim 1 wherein the acid with a pKa<+3 comprises trifluoromethanesulfonic acid.

10. The process according to claim 2 wherein the mixture of at least two acids comprises trifluoromethanesulfonic acid and an acid having a pKa between −3 and +3 selected from a sulfonic acid.

11. The process according to claim 1 wherein the ratio moles of mono tert-phosphine:moles of acid is about 1.05:1 to about 5:1.

* * * * *